United States Patent [19]
Kacian et al.

[11] Patent Number: 5,916,777
[45] Date of Patent: Jun. 29, 1999

[54] ENZYMATIC SYNTHESIS OF OLIGONUCLEOTIDES USING 3'-RIBONUCLEOTIDE PRIMERS

[75] Inventors: Daniel Louis Kacian; Nanibhushan Dattagupta; David Bruce Lackey, all of San Diego, Calif.

[73] Assignee: Gen-Probe Incorporated, San Diego, Calif.

[21] Appl. No.: 08/949,076

[22] Filed: Oct. 10, 1997

Related U.S. Application Data

[63] Continuation of application No. 08/477,228, Jun. 7, 1995, abandoned.

[51] Int. Cl.$^6$ .............. C12Q 1/68; C12P 19/34; A01N 43/04; C07H 21/04
[52] U.S. Cl. .............. 435/91.1; 435/6; 435/91.2; 514/44; 536/24.3; 536/24.33; 536/25.3
[58] Field of Search ............ 435/6, 91.1, 91.2; 514/44; 536/24.3, 24.33, 25.3

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,786,600 | 11/1988 | Kramer et al. | 435/235 |
| 4,800,159 | 1/1989 | Mullis et al. | 435/172.3 |
| 4,851,330 | 7/1989 | Kohne | 435/6 |
| 4,994,368 | 2/1991 | Goodman et al. | |
| 5,030,557 | 7/1991 | Hogan et al. | 435/6 |
| 5,035,996 | 7/1991 | Hartley | 435/6 |
| 5,212,295 | 5/1993 | Cook | 536/26.7 |
| 5,264,423 | 11/1993 | Cohen et al. | 514/44 |
| 5,276,019 | 1/1994 | Cohen et al. | 514/44 |
| 5,286,717 | 2/1994 | Cohen et al. | 514/44 |
| 5,288,611 | 2/1994 | Kohne | 435/6 |
| 5,418,149 | 5/1995 | Gelfand et al. | |
| 5,427,929 | 6/1995 | Richards et al. | 435/91.21 |
| 5,436,143 | 7/1995 | Hyman | 435/91.1 |
| 5,470,967 | 11/1995 | Huie et al. | 536/24.3 |

FOREIGN PATENT DOCUMENTS

| | | |
|---|---|---|
| 0427073 | 5/1991 | European Pat. Off. |
| 0496483 | 7/1992 | European Pat. Off. |
| 8810315 | 12/1988 | WIPO |
| 8901050 | 2/1989 | WIPO |
| 8902439 | 3/1989 | WIPO |
| 9101384 | 2/1991 | WIPO |
| 9205287 | 4/1992 | WIPO |
| 9308296 | 4/1993 | WIPO |
| 9322461 | 11/1993 | WIPO |
| 9403472 | 2/1994 | WIPO |
| 9503407 | 2/1995 | WIPO |
| 9619572 | 6/1996 | WIPO |

OTHER PUBLICATIONS

Olsen et al. "Investigation of the Inhibitory Role of Phosphorothioate Internucleotidic Linkages on the catalytic Activity of the Restriction Endonuclease EcoRV" Biochemistry, vol. 29, pp. 9546–9551, 1990.

Potter & Eckstein, "Cleavage of Phosphorothioate–substituted DNA by Restriction Endonucleases", The Journal of Biological Chemistry, 259 (23):14243–14248, (1984).

(List continued on next page.)

Primary Examiner—Ardin H. Marschel
Assistant Examiner—Jezia Riley
Attorney, Agent, or Firm—Charles B. Cappellari; Carlos A. Fisher

[57] ABSTRACT

The present invention relates to methods of enzymatically synthesizing oligonucleotides. In particular, it relates to the use of 3'-ribonucleotide primers which effectively serve to initiate oligonucleotide synthesis, and can also be easily cleaved from synthesis products and reused in subsequent synthesis reactions.

38 Claims, 7 Drawing Sheets

OTHER PUBLICATIONS

Vosberg & Eckstein, "Effect of Deoxynucleoside Phosphorothioates Incorporated in DNA on Cleavage by Restriction Enzymes", The Journal of Biological Chemistry, 257 (11):6595–6599, (1982).

Bartlett, et al. Stereochemical course of polymerization catalyzed by avian myeloblastosis virus reverse transcriptase. *The Journal of Biological Chemistry.* 257:8879–8884. U.S.A. (1982).

Bergot, et al. The manufacture and molecular characterization of phosphorothioate deoxynucleotides for use as antisense therapeutics in human clinical trials. *Nucleic Acids Symposium Series.* 29:57. Oxford University Press, Oxford, U.K. (1993).

Biggin, et al. Buffer gradient gels and S label as an aid to rapid DNA sequence determination. *Proc. Nat.l Acad. Sci. USA.* 80:3963–3965. Biochemistry, (1983).

Brody, et al. Stereochemical course of nucleotidyl transfer catalyzed by bacteriophage T77 induced DNA polymerase. *Biochemistry.* 21:2570–2572. (1982).

Brown, T., et al. Modern machine–aided methods of oligodeoxyribonucleotidesynthesis. *Oligonucleotides and Analogues: A Practical Approach.* 1–25. IRL Press, Oxford, U.K. (1991).

Burgers, et al. A study of the mechanism of DNA polymerase I from *EScherichia coli* with diasteromeric phosphorothioate analogs of deoxyadenosine triphosphate. *The Journal of Biological Chemistry.* 254:6889–6893. U.S.A. (1979).

Dyatkina, et al. *Nucleic Acids Research.* 238. Oxford University Press, Oxford, England (1991).

Eckstein, et al. Nucleotide Phosphorothioates. 54:367–402. Ann. Rev. Biochem., (1985).

Leiter, et al. Inhibition of influenza virus replication by phosphorothioate oligodeoxynucleotides. *Proc. Nat'l Acad. Sci. USA.* 87:3430–3434. Microbiology, (1990).

Matsukara, et al. Synthesis of phosphorothioate analogues of oligodeoxyribonucleotides and their antiviral activity against human immunodeficiency virus (HIV). *Gene* 72:343–347. (1988).

McGilvery, R., et al. Changes in the Genetic Message. *Biochemistry. A functional approach.* 3:125–126. W.B. Saunders Company, Philadelphia, London, Toronto, Mexico City, Rio de Janeiro, Syndey, Tokyo, (1983).

Mullis, et al. Specific synthesis of DNA in vitro via a. polymerase–catalyzed chain reaction. *Methods in Enzymology*, 155:335–350. Academy Press, Inc. (1987).

Murakawa, et al. Laboratory Methods. Direct detection of HIV–1 RNA from AIDS and ARC patient samples. *DNA.* 7:287–295. Mary Ann Liebert, Inc., Publishers (1988).

Romaniuk, et al. A study of the mechanism of T4 DNA polymerase with diaseromeric phosphorothioate analogues of deoxyadenosine triphosphate. *The Journal of Biological Chemistry.* 257:7684–7688. U.S.A. (1982).

Sinha, D. Large–Scale oligonucleotide synthesis using the solid–phase approach. *Methods in Molecular Biology: Protocols for Oligonucleotides and Analogs.* 20:437–463. Humane Press Inc., Totowa, N.J. (1993).

Stec, W., et al. Novel route to oligo(deoxyribonucleotide phosphorothioates). Stereocontrolled synthesis of P–chiral oligo(deoxyribonucleotide phosphorothioates). *Nucleic Acids Research.* 19:5883–5888. Oxford University Press, Oxford, U.K. (1991).

Stec, W., et al. Automated solid–phase synthesis, separation, and stereochemistry of phosphorothioate analogues of oligodeoxyribonucleotides. *J. Am. Chem. Soc.* 106:6077–6079. American Chemical Society, (1984).

Taylor, et al. The use of phosphorotioate–modified DNA in restriction enzyme reactions to prepare nicked DNA. *Nucleic Acids Research.* 13:8749–8764. IRL Press Limited, Oxford, England (1985).

Degradation and modification of nucleic acids. Chapter 4, *Biochemistry of the Nucleic Acids.* 97–108, (Adams, et al., ed. 11th ed. 1992).

Olsen, et al., "Interaction of Restriction Endonucleases With Phosphorothioate–Containing DNA", Nucleosides & Nucleotides, 10(1–3):665–667 (1991).

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:

(A) LENGTH: 90 base pairs
            (B) TYPE: nucleic acid
            (C) STRANDEDNESS: single
            (D) TOPOLOGY: linear (xi) SEQUENCE DESCRIPTION: SEQ ID NO:1:

GAAGCCCGGA CAGCCCAGGG GAGCCCGGCC AGGCGCTCGA GAAGCCCGGA CAGCCCAGGG        60

GAGCCCTCGC CTATTGTTAA AGTGTGTCCT                                        90

(2) INFORMATION FOR SEQ ID NO:2:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:2:

CCCGAGGGGA CCCGACAGGC CCGAAG                                            26

(2) INFORMATION FOR SEQ ID NO:3:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:3:

TATAGTGAGT CGTATTATTT TTAATACGAC TCACTATA                               38

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:4:

GACGGCACCT CTTCGGGCCT GTCGGGTCCC CTCGGGCCC                              39

(2) INFORMATION FOR SEQ ID NO:5:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:5:

GACGGCACCT CTTCGGGCCT GTCGGGTCCC CTCGGGCCCT ATAGTGAGTC GTATTATTTT        60

TAATACGACT CACTATA                                                      77

(2) INFORMATION FOR SEQ ID NO:6:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:6:

GGGCCCGAGG GGACCCGACA GGCCCGAAGA GGTGCCGTC                              39

(2) INFORMATION FOR SEQ ID NO:7:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:7:

AGGTGCCGTC                                                              10

(2) INFORMATION FOR SEQ ID NO:8:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO:8:

GGGCCCGAGG GGACCCGACA GGCCCGAAG                                         29

(2) INFORMATION FOR SEQ ID NO:9:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (xi) SEQUENCE DESCRIPTION: SEQ ID NO:9:

GACGGCACCU C                                                            11

(2) INFORMATION FOR SEQ ID NO:10:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:10:

GACGGCACCT CTTCGGGCCT GTCGGGTCCC CTCGGGCCC                              39

(2) INFORMATION FOR SEQ ID NO:11:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO:11:

CTTCGGGCCT GTCGGGTCCC CTCGGGCCC                                         29

(2) INFORMATION FOR SEQ ID NO:12:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:12:

TATAGTGAGT CGTATTATTT TTAATACGAC TCACTATAGC                             40

(2) INFORMATION FOR SEQ ID NO:13:

(i) SEQUENCE CHARACTERISTICS:

(A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO:13:

AAAAAAAAAA GCTTTCGTTT TTTTTTTCTT CGGGCCTGTC GGGTCCCCTC GGGGC      55

(2) INFORMATION FOR SEQ ID NO:14:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (xi) SEQUENCE DESCRIPTION: SEQ ID NO:14:

AAAAAAAAAA GCTTTCGTTT TTTTTTTCTT CGGGCCTGTC GGGTCCCCTC GGGGCTATAG   60

TGAGTCGTAT TATTTTTAAT ACGACTCACT ATAGC                              95

(2) INFORMATION FOR SEQ ID NO:15:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO:15:

GCCCCGAGGG GACCCGACAG GCCCGAAGAA AAAAAAACG AAAGCTTTTT TTTTT          55

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:16:

GCCCCGAGGG GACCCGACAG GCCCGAAG                                       28

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:17:

AAAAAAAAAA CGAAAGCUUU UUUUUUU                                        27

(2) INFORMATION FOR SEQ ID NO:18:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:18:

GGGACCCGAC AGGC                                                      14

(2) INFORMATION FOR SEQ ID NO:19:

(i) SEQUENCE CHARACTERISTICS:

```
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:19:

TATAGTGAGT CGTATTATTT TTAATACGAC TCACTATAGC                      40

(2) INFORMATION FOR SEQ ID NO:20:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (xi) SEQUENCE DESCRIPTION: SEQ ID NO:20:

TTTTTTTTTT GGCCGCCTGT CGGGTCCCGG CCGCCTGTCG GGTCCCGGCC GCCTGTCGGG     60

TCCCGGCCGC                                                           70

(2) INFORMATION FOR SEQ ID NO:21:

(i) SEQUENCE CHARACTERISTICS:
            (A) LENGTH: 110 base pairs
            (B) TYPE: nucleic acid
            (C) STRANDEDNESS: single
            (D) TOPOLOGY: linear (xi) SEQUENCE DESCRIPTION: SEQ ID NO:21:

TTTTTTTTTT GGCCGCCTGT CGGGTCCCGG CCGCCTGTCG GGTCCCGGCC GCCTGTCGGG     60

TCCCGGCCGC TATAGTGAGT CGTATTATTT TTAATACGAC TCACTATAGC              110

(2) INFORMATION FOR SEQ ID NO:22:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (xi) SEQUENCE DESCRIPTION: SEQ ID NO:22:

GCGGCCGGGA CCCGACAGGC GGCCGGGACC CGACAGGCGG CCGGGACCCG ACAGGCGGCC     60

(2) INFORMATION FOR SEQ ID NO:23:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:23:

CCGGGACCCG ACAGGCGG                                                  18
```

ENZYMATIC SYNTHESIS OF OLIGONUCLEOTIDES USING 3'-RIBONUCLEOTIDE PRIMERS

This application is a continuation of U.S. application Ser. No. 08/477,228, filed Jun. 7, 1995, entitled 'Enzymatic Synthesis of Oligonucleotides Using 3'-Ribonucleotide Primers,' now abandoned."

FIELD OF THE INVENTION

The present invention relates to methods of enzymatically synthesizing oligonucleotides. In particular, it relates to the use of 3'-ribonucleotide primers which effectively serve to initiate oligonucleotide synthesis, and can also be easily cleaved from synthesis products and regenerated for use in subsequent synthesis reactions.

BACKGROUND OF THE INVENTION

Nucleic acids are linear polymers consisting of individual nucleotide subunits which are covalently linked together via phosphodiester bonds. Oligonucleotides are now widely used in the biomedical field as nucleic acid sequencing primers, diagnostic probes and modulators of gene function. One of the most promising uses of oligonucleotides is in the field of antisense therapeutics.

Oligonucleotides can be conveniently synthesized using enzymatic or chemical methods, with the latter generally providing for larger scale production than the former. One of the most widely used methods of chemically synthesizing oligonucleotides is based on phosphoramidite solid-phase chemistry (See *Methods in Molecular Biology,* Volume 20: *Protocols for Oligonucleotides and Analogs,* S. Agrawal editor, Humana Press Inc., Totowa, N.J., 437–463 (1993)) Now fully automated, this method can be used to chemically produce oligonucleotides in commercial quantities. (See *Oligonucleotides and Analogues: A Practical Approach.* Edited by F. Eckstein, I.R.L. Press, Oxford, England, 1–24 (1991).)

Despite the convenience of chemical synthesis, the number of steps and the harshness of the chemicals involved leads to the formation of a product which may contain toxic chemical impurities, such as damaged nucleotide bases. Because the level of impurities is normally relatively low, chemically synthesized oligonucleotides are still suitable for use in many different applications. However, certain applications require a product which is substantially free of chemical impurities. In particular, when the application involves a biological system, the presence of chemical impurities can have a deleterious effect. Moreover, when the application involves an in vivo therapeutic agent, chemical purity is essential. Enzymatic synthesis, which can be used to produce an oligonucleotide product in an aqueous solution that is essentially free of toxic chemical impurities and hazardous byproducts is thus preferred for these applications.

The use of oligonucleotides in biological systems is also compromised by the presence of nucleases which catalyze the breakdown of nucleic acids by hydrolysis of phosphodiester bonds (See *The Biochemistry of the Nucleic Acids:* Chapter 4, *Degradation and Modification of Nucleic Acids,* Roger L. P. Adams et al., Chapman & Hall, London, England, 97–108 (1992)). Such a breakdown can cause a significant reduction in the biological activity of oligonucleotides in vivo thus resulting in diminished therapeutic effectiveness. This degradation can be controlled by modifying or substituting the phosphodiester bonds with a more nuclease-resistant analog, such as phosphotriester, phosphorothioate or methylphosphonate.

Phosphorothioate-containing oligonucleotides efficiently resist degradation by many nucleases, and are thus preferred for use in some biological systems. Phosphorothioate linkages have a sulfur in place of oxygen as one of the non-bridging atoms bonded to phosphorous. This substitution produces chirality at the phosphorous which is designated as having either the Rp or Sp diastereomer orientation. Since the chiral orientation is an important factor which influences duplex structure, enzyme recognition, conformation and/or hybridization kinetics, it is desirable to use chirally pure phosphorothioate-containing oligonucleotides. Other modified oligonucleotides such as those containing phosphotriester and methylphosphonate linkages also contain a substitution of one of the oxygen atoms bonded to phosphorous and thus exist as diastereomers.

Chemical synthesis of phosphorothioate-containing oligonucleotides generally lacks stereoselectivity and results in the formation of a product which is a heterogeneous mixture of two different chiral species. Attempts to stereochemically control the synthesis of chirally pure oligonucleotides have met with mixed success (Stec, et al., Nucleic Acids Research, 19(21): 5883–5888 (1991)). Cook (U.S. Pat. No. 5,212,295) has described the chemical synthesis of modified oligonucleotides with greater than 75% chiral purity. In comparison, enzymatic synthesis of phosphorothioate-containing oligonucleotides can be used to produce chirally pure product, since several polymerases form only phosphorothioate linkages having the Rp orientation (Eckstein, Ann. Rev. Biochem. 54: 367–402 (1985)).

The enzymatic synthesis of other modified oligonucleotides is also well known in the art. Methylphosphonate-containing oligonucleotides can be produced enzymatically using DNA polymerases α and ε from human placenta, DNA polymerase β from rat liver, and reverse transcriptases from HIV and avian myeloblastosis virus (Dyatkina, et al., Nucleic Acids Research Symposium Series 24: 238 (1991)).

The economical enzymatic synthesis of any oligonucleotide, whether modified or not, depends on the ability to efficiently utilize the components of the synthesis reaction to form a product which is sufficiently pure for its intended use. In some instances, it is desirable to use synthesis components which are capable of functioning repeatedly and are thus "reusable". For example, Richards et al. (PCT WO 92/05287) describes the use of reusable synthesis templates which function repeatedly in the same synthesis reaction. In other instances, it may be desirable to use synthesis components which function only once in a synthesis reaction and are thereafter degraded or rendered nonfunctioning. Walder, et al. (European Patent Application 496,483 A2) describe the use of RNA-containing primers that are cleaved in order to prevent the formation of undesired amplification products in subsequent synthesis reactions.

Even though many of the prior art methods are suitable for use in the enzymatic synthesis of oligonucleotides, large scale synthesis of chirally pure oligonucleotides has yet to be optimized. It is therefore an object of the present invention to provide for the economical synthesis of oligonucleotides which are chirally pure.

The present invention describes a convenient and economical method of enzymatically synthesizing oligonucleotides. By utilizing 3'-ribonucleotide primers, separation of enzymatically synthesized oligonucleotides from primers is greatly facilitated and allows for regeneration of functional primers which can then be used in subsequent synthesis reactions.

None of the references herein are admitted to be prior art.

SUMMARY OF THE INVENTION

The present invention provides a method of enzymatically synthesizing oligonucleotides using 3'-ribonucleotide primers which can be cleaved and reused in subsequent synthesis reactions. The present method includes generally the steps of: (a) providing a nucleic acid template, the template comprising a primer binding region and an oligonucleotide complementary region; (b) contacting the template with a nucleic acid primer able to hybridize to the template to form a template-primer hybrid, wherein the primer comprises DNA with at least one ribonucleotide at or near its 3'-terminus; (c) incubating the template-primer hybrid in the presence of at least one DNA polymerase under conditions in which DNA synthesis occurs to form a primer extension product; (d) cleaving the primer extension product to separate the primer from the oligonucleotide or oligonucleotides by hydrolyzing the phosphate linkage(s) in the 3' direction from the ribonucleotide(s); and (e) repeating steps (b) and (c) at least once with the primer from step (d).

The template can be either DNA or RNA, but for ease of digestion is preferably RNA. Each template is composed of two regions: a primer binding region and an oligonucleotide complementary region. The oligonucleotide complementary region may contain two or more subregions, each of which can have the same or a different nucleic acid sequence, such that each subregion directs the synthesis of an individual oligonucleotide. In this manner, oligonucleotides having the same or different lengths and/or sequences may be formed from the same template.

The 3'-ribonucleotide primers consist of DNA with at least one ribonucleotide residue at or near their 3'-terminus. When used as primers in the enzymatic synthesis of oligonucleotides, they form at least one cleavable nucleotide linkage between the primer and the synthesis product which serves as a convenient cleavage site for separation of the primer from the synthesis product. Preferably, the 3'-ribonucleotide primers contain a single ribonucleotide at the 3' terminus.

The template-primer hybrid directs the synthesis of a primer extension product via sequential addition of nucleotides or modified nucleotides. The use of modified nucleotides is preferred for formation of modified oligonucleotides which are nuclease-resistant.

Cleavage of the primer extension product to separate the primer from the oligonucleotide product can be accomplished using alkaline hydrolysis and/or RNase. If necessary, the 3'-OH terminus of the primer can be regenerated using phosphatase, and the primer can be used in a subsequent synthesis reaction.

Additionally, when the template's oligonucleotide complementary region contains two or more subregions which are each designed to direct the synthesis of an individual oligonucleotide, incorporation of restriction sequences into the primer extension product can be used to position cleavage sites between the individual oligonucleotides. Cleavage to separate the individual oligonucleotides from each other can then be accomplished using the appropriate restriction endonuclease.

If digestion of the template is used to separate the primer extension product from the template, cleavage to separate the primer from the oligonucleotide product and, if necessary, the individual oligonucleotides from each other, can take place before, during or after template digestion. Digestion of an RNA template can be accomplished via alkaline hydrolysis and/or an appropriate Rnase. Digestion of a DNA template can be accomplished by using an appropriate DNase.

BRIEF DESCRIPTION OF THE DRAWINGS

As used in the Figures described below, the abbreviations will have the following meaning.

pbr=primer binding region
ocr=oligonucleotide complementary region
sr=subregion
cs=cleavage site
scr=self-complementary region
R=ribonucleotide FIG. 1a, b, and c illustrate several different template structures, each containing a primer binding region and an oligonucleotide complementary region.

DESCRIPTION OF THE PREFERRED EMBODIMENTS

Figure 1A:
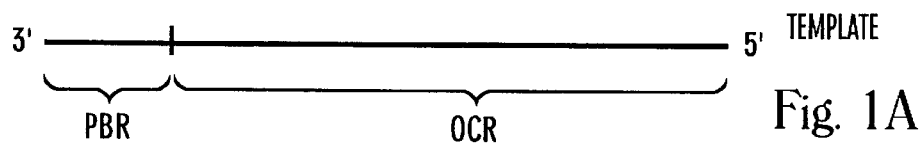

The present invention concerns the enzymatic synthesis of oligonucleotides using 3'-ribonucleotide primers. In order to more clearly describe the subject matter of the present invention, certain terms used herein shall be defined as follows unless otherwise indicated:

Chirally pure: "Chirally pure", when used to refer to a phosphorothioate-containing oligonucleotide, means that the oligonucleotide contains only Rp or Sp diastereomers.

Cleavage Site: "Cleavage site" means a location in a nucleic acid that is susceptible to hydrolysis of at least one native or modified phosphodiester bond in the sugar-phosphate backbone of the nucleic acid. When used to refer to a restriction endonuclease recognition sequence, the term "cleavage site" means the cleavable linkage (denoted as "/") in a sequence of nucleotides which are specifically recognized by a restriction endonuclease which binds to the sequence to effectuate cleavage. For example, the sequence GGCC is recognized by Hae III and cleavage occurs at GG/CC. "Cleavage site", as used herein, can also mean the linkage 3' to a ribonucleotide residue, which is susceptible to cleavage by an agent such as RNase or alkali.

Cleave: "Cleave" means to cause a break in the sugar-phosphate backbone of an oligonucleotide using an endonuclease or other cutting agent.

Complementary: "Complementary", when used to refer to a nucleic acid, means a nucleic acid of one polarity containing a sequence of nucleotides whose bases pair with the nucleotide bases of another nucleic acid of opposite polarity, i.e. adenine ("A") pairs with thymine ("T") or uracil ("U"), and guanine ("G") pairs with cytosine ("C"). For example, a nucleic acid having the sequence GCAU in the 5' to 3' direction is "complementary" to a nucleic acid having the sequence CGTA in the 3' to 5' direction. Use of the term complementary herein is intended to include those nucleic acids which are substantially complementary. Complementary nucleic acids can also be referred to as one being the plus ("(+)") or "sense" strand and the other being the minus ("(−)") or "antisense" strand.

Diastereomer: "Diastereomer" means a chiral compound that can exist as two different chiral species which, in the case of phosphorothioate-containing oligonucleotides, depends on the orientation of sulfur in relation to the chiral phosphorous. The two possible orientations are Rp and Sp, thus the chiral species are referred to as being Rp or Sp diastereomers.

Digestion: "Digestion" means the degradation of a nucleic acid into its individual nucleotides (complete digestion) or into short segments (partial digestion).

dNTP: "dNTP" means a deoxynucleoside triphosphate, wherein N refers to the nucleotide bases, i.e. dATP means deoxyadenosine triphosphate, dCTP means deoxycytosine triphosphate, etc. The term "dNTP", or "nucleotide", is intended to include an unmodified deoxynucleoside triphosphate, as well as a deoxynucleoside triphosphate with a modified α linkage, such as deoxynucleoside triphosphorothioate and deoxynucleoside methylphosphonate.

dNTPαS: "dNTPαS" means a deoxynucleoside triphosphates having a sulfur atom substituted for oxygen at the alpha phosphorous position wherein N is defined as described for dNTP.

Figure 4:
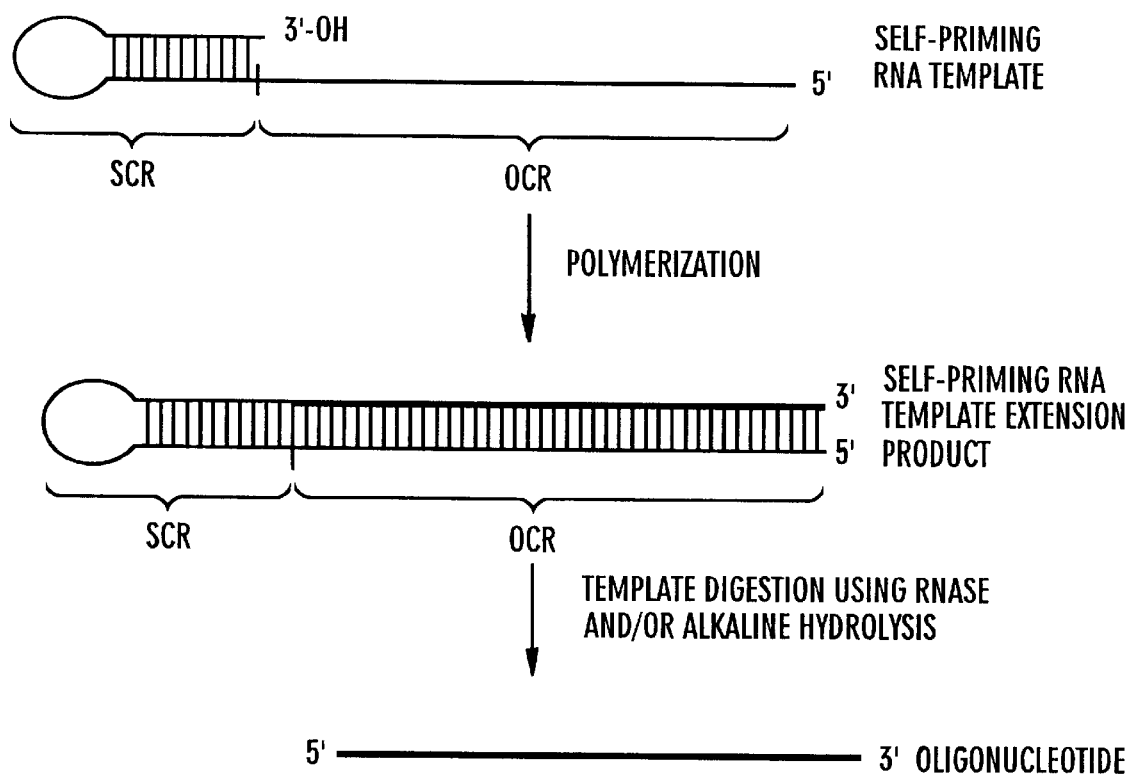
FIG. 4 illustrates the enzymatic synthesis of an oligonucleotide using a self-priming template.

Hairpin: "Hairpin" means the looped self-hybridized structure that a self-priming template takes when the two intra-complementary regions, which are separated by a non-complementary region that becomes the "loop", form a duplex. See FIG. 4.

Hybridization: "Hybridization" means the formation of a stable duplex between nucleotide sequences that are substantially complementary.

Modified: "Modified", when used to refer to a nucleic acid, means a nucleic acid in which any of the natural structures have been altered. These include the native phosphodiester linkages (also referred to herein as simply "phosphodiester linkages"), the sugars (ribose in the case of RNA or deoxyribose in the case of DNA) and/or the purine or pyrimidine bases. Modified phosphodiester linkages include phosphorothioates, phosphotriesters, methylphosphonates and phosphorodithioates.

Nucleic Acid Sequence: "Nucleic acid sequence", or "sequence", means both a nucleic acid having a particular sequence of nucleotides, and also the sequence or order of nucleotides present in a particular nucleic acid. Which of these two meanings applies will be apparent from the context in which this term is used.

Oligonucleotide: "Oligonucleotide" means a relatively short segment of a nucleic acid polymer. Although a limitation to any preise length is not intended, oligonucleotides are generally between 8 to 100 nucleotides in length.

Polarity: "Polarity" means the orientation of a nucleic acid polymer which is created when the C3 position of one deoxyribose (or ribose) moiety is linked together with the C5 of the adjacent deoxyribose (or ribose) moiety via a native or modified phosphodiester linkage. Polarity is created by the sequence of bases relative to the 5' and 3' ends. Two complementary strands are of "opposite polarity" when the sequence of bases read from the 5' to 3' direction of one strand and the sequence of bases read from the 3' to 5' direction of the other give corresponding Watson and Crick base paris at each position.

Phosphorothioate oligonucleotide: "Phosphorothioate oligonucleotide" means an oligonucleotide having all phosphorothioate linkages (also referred to as a "fully phosphorothioated oligonucleotide").

Phosphorothioate-containing oligonucleotide: "Phosphorothioate-containing oligonucleotide" means an oligonucleotide having at least one but less than all phosphorothioate linkages (also referred to as a "partially phosphorothioated oligonucleotide").

Polymerase: "Polymerase" means an enzyme which is capable of catalyzing the synthesis of a complementary copy of a nucleic acid template, which in the case of a DNA polymerase is brought about by the sequential addition of deoxynucleotides to a primer.

Primer: "Primer" means an oligonucleotide that is complementary to a template that hybridizes with the template to give a template-primer hybrid for initiation of synthesis by a DNA polymerase, such as reverse transcriptase or bacteriophage T4 DNA polymerase, and which is extended by the sequential addition of covalently bonded nucleotides linked to its 3' end that are complementary to the template. The result is the formation of a primer extension product.

RNase H: "RNase H" means an enzyme that degrades the RNA strand of an RNA:DNA duplex.

Self-priming template: "Self-priming template" means a template which is capable of initiating synthesis by a polymerase without the addition of a separate primer. The 3'-terminus of a self-priming template serves as the primer.

Self-Priming Template Extension Product: "Self-priming template extension product" means the product which is formed during oligonucleotide synthesis using a self-priming template. As used herein, a self-priming template extension product is a type of primer extension product to which the template remains covalently attached after synthesis.

Substantially Complementary: "Substantially Complementary", when used to refer to a nucleic acid, means having a sequence such that not all of the nucleotides exhibit base pairing with the nucleotides of another nucleic acid, but the two nucleic acids are nonetheless capable of forming a stable hybrid under specified conditions.

Template: "Template" means a nucleic acid molecule that is able to be copied by a polymerase, and which has a sequence of nucleotides which will provide the pattern and serve as substrate for producing a desired oligonucleotide. In order to serve as such, the template must contain a sequence which is capable of hybridizing with a primer (a "primer binding region"). A self-priming template must contain a sequence which is capable of forming a hairpin structure (a "self-complementary region").

Template precursor: "Template precursor" means an oligonucleotide which contains at least one copy of the template nucleic acid sequence and can be cleaved to produce at least one template nucleic acid.

Template-primer hybrid: "Template-primer hybrid" means a partially double-stranded nucleic acid which is formed when a template and a primer hybridize.

Oligonucleotides have many different uses in biomedical science. To name a few, they can be used as labelled probes for detection of specific nucleic acid sequences in diagnostic assays (Kohne et al., U.S. Pat. Nos. 4,851,330 and 5,288,611); they can be used to promote formation of regions in an RNA target which are accessible to hybridization of labelled probes (See Hogan et al., U.S. Pat. No. 5,030,557); they can be used as investigational tools for the sequencing of DNA (Biggin et al., P.N.A.S. 80: 3936–3965 (1983); and, especially in the case of modified oligonucleotides, they can be used in biological systems. Because of the ability of certain modified nucleic acids to resist degradation by nucleases, they are much more stable in such systems than their unmodified (native) phosphodiester counterparts. This makes them ideal for use in vivo as antisense therapeutic agents.

"Antisense" refers to the use of oligonucleotides as regulators of gene function. An antisense oligonucleotide, i.e. an oligonucleotide having a nucleic acid sequence which is complementary to that of the "sense" nucleic acid to which it is targeted, can function in many different ways to modulate gene function. When the targeted nucleic acid is messenger RNA ("mRNA"), it may function by preventing translation of the mRNA into protein or inhibiting binding of ribosomes. When the targeted nucleic acid is DNA, it may prevent transcription into mRNA.

The use of phosphorothioate-containing oligonucleotides in the field of antisense therapeutics is now widespread. Examples of a few of the applications are: the treatment of acute myeloblastic leukemia (Bergot, et al., Nucleic Acids Symposium Series No. 29, pg. 57 (1993)); the inhibition of HIV replication (Matsukura et al., Gene 72: 343–347 (1988)); and the inhibition of influenza virus replication (Leiter et al., P.N.A.S. 87: 3430–3434 (1990) and Cohen et al., U.S. Pat. Nos. 5,264,423; 5,276,019; and 5,286,717).

Oligonucleotides which are useful for particular purposes can be "designed" to hybridize with selected portions of a target sequence and, by varying such things as length and target binding region, their suitability for certain purposes can be maximized. For example, if the desired oligonucleotide product is an antisense therapeutic to be used in targeting the protein coding region of mRNA, an oligonucleotide might be chosen which would be complementary to an accessible region of the mRNA sequence, i.e. one expected not to contain secondary structure, with sufficient length and complementarity to a unique sequence so as to not exhibit cross-reactivity with non-targeted nucleic acids.

Although appropriate oligonucleotide length depends entirely on the particular use for which the oligonucleotide is designed, certain generalizations are possible. If the oligonucleotide is to be used as a linker in cloning, it will preferably be between about 6 and 60 nucleotides in length. If it is to be used as a sequence-specific hybridization probe, it will preferably be between 12 and 60 nucleotides in length. If it is to be used as a polymerase chain reaction ("PCR") primer, it will preferably be between about 8 and 35 bases. If it is to be used as a ligase chain reaction ("LCR") primer, it will preferably be between about 8 and 35 nucleotides in length. If it is to be used as an antisense therapeutic agent, it will preferably be between about 12 and 50, and more preferably between about 15 and 30 nucleotides in length.

The present invention is particularly well-suited for use in enzymatically synthesizing phosphorothioate oligonucleotides which are chirally pure. It generally involves the use of templates and primers to form template-primer hybrids (or the use of self-priming templates to form hairpins), the synthesis of primer extension products, and the cleavage and separation of the desired individual oligonucleotides. Each of these aspects are more fully described below.

The Template

The template can be either DNA or RNA, or modified DNA or RNA, but is preferably unmodified RNA to facilitate digestion. Templates having a specific nucleic acid sequence can be prepared using any known chemical or enzymatic methods. In addition, templates can be prepared using any known recombination or cloning methods, such as with plasmids, M13 DNA, etc. Chemical synthesis can be conveniently performed according to the method described by Stec et al. (J. Am. Chem. Soc. 106: 6077–6079 (1984)) using the phosphoroamidite method and an automated synthesizer, such as Model 380-B (Applied Biosystems, Inc., Foster City, Calif.).

Particularly useful methods for synthesizing templates are based on enzymatic amplification technologies for producing multiple copies from as few as a single copy of a nucleic acid. The following references, which are incorporated herein in their entirety, are representative of several different amplification procedures which can be employed for production of template. PCR for the production of DNA is described by Mullis, et al. (See U.S. Pat. Nos. 4,683,195; 4,683,202; and 4,800,159, and Methods in Enzymology, Volume 155, 1987, pp. 335–350.) A Qβ replicase-based amplification system for producing RNA is described by Kramer, et al., in U.S. Pat. No. 4,786,600.

Because single-stranded template preparation lacking complementary strands are ideal, preferred amplification procedures utilize transcription-based amplification systems, which produce multiple copies of single-stranded RNA from double-stranded DNA. (See Burg, et al., WO 89/01050 and Gingeras, et al., WO 88/10315.) Still other transcription-based amplification methods are described by Kacian, et al. (WO 91/01384 and WO 93/22461) and McDonough, et al., (WO 94/03472). PCR has also been used to produce single-stranded RNA from double stranded DNA from which RNA is synthesized in vitro using DNA-directed RNA polymerase. (See Murakawa, et al., DNA 7: 287–295 (1988)).

Figure 1B:
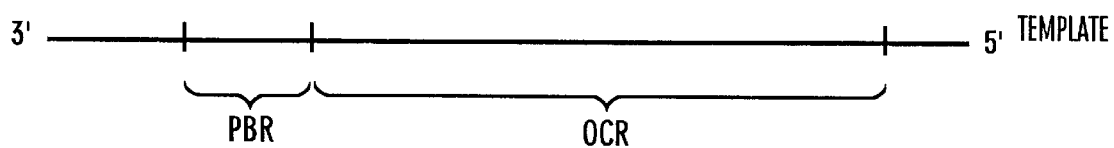
Figure 1C:
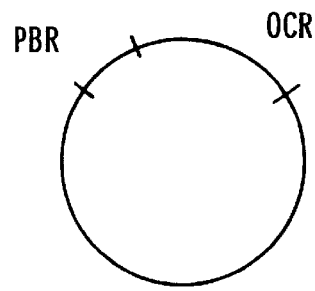

The nucleic acid sequence of a template will necessarily have at least two nucleic acid subsequences; one of which is complementary to the primer, i.e. the "primer binding region", and another of which is complementary to the oligonucleotide product to be synthesized, i.e. the "oligonucleotide complementary region". In addition, the template can be in the form of a plasmid, or a PCR product (after denaturation and strand separation), or restriction fragments or linearized versions thereof. For examples of different template structures, see FIG. 1.

Figure 2A:
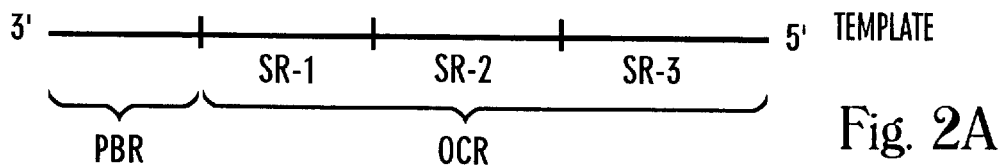
FIG. 2a, b, and c illustrate several different template structures, each containing a primer binding region, and an oligonucleotide complementary region which consists of three separate subregions.
Figure 2B:
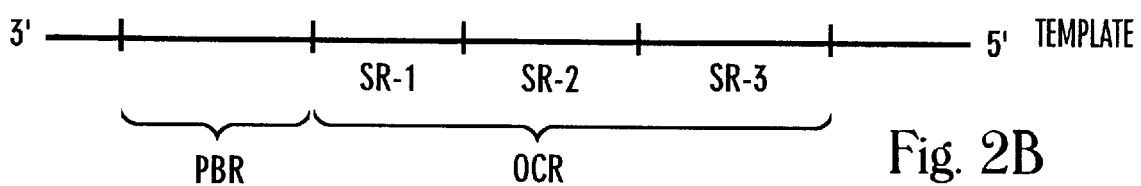
Figure 2C:
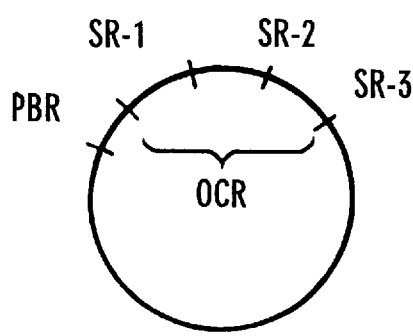

In order to use a single template for the production of more than one oligonucleotide, a template is synthesized which contains an oligonucleotide complementary region having more than one subregion, such that each subregion is complementary to and capable of directing the synthesis of an individual oligonucleotide. See FIG. 2. Using such a template, the oligonucleotide complementary region is complementary to and directs the synthesis of an "oligonucleotide product", which can then be cleaved after synthesis to separate the individual oligonucleotides.

A template with more than one such subregion must also be designed to facilitate separation of the individual oligonucleotides from each other after synthesis. This can be accomplished by incorporating restriction sequences into the primer extension product which are specifically positioned to allow for cleavage to separate the individual oligonucleotides. (See Cleavage of the Primer-Extension Product below for a more complete description of cleavage to separate individual oligonucleotides.)

The individual oligonucleotides synthesized in this manner may have the same or different sequences, as well as the same or different lengths. This method is very useful when pairs of oligonucleotides which do not require further separation are to be used for a particular application.

Figure 3:
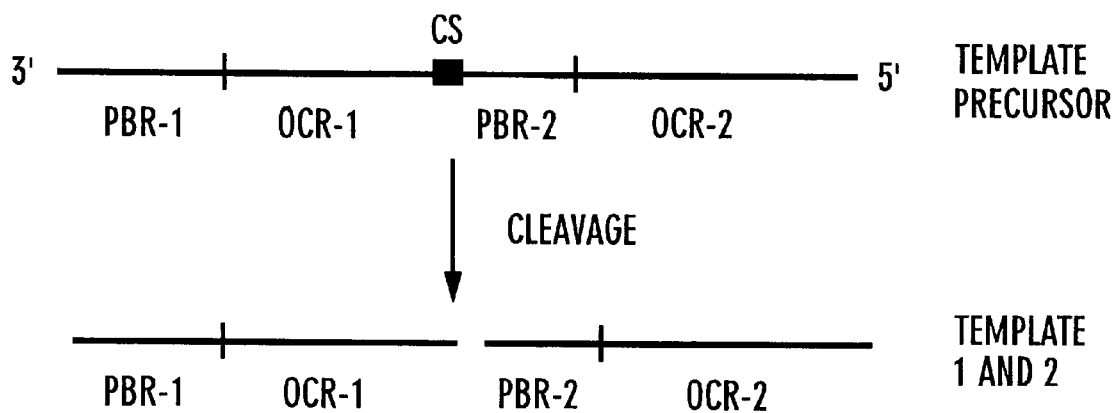
FIG. 3 illustrates the use of a template precursor which is cleaved to form two separate templates.

The template can be formed such that it is ready for use in the synthesis of oligonucleotides, or it can be formed as a template precursor which can then be converted to a usable template by cleavage with an endonuclease or other such cleavage mechanism. (See Cleavage of the Primer-Extension Product below for a complete description of cleavage mechanisms.) See FIG. 3.

Additionally, templates can be self-priming, i.e. capable of initiating synthesis without the need for a separate primer. Instead of a primer binding region, a self-priming template has a "self-priming region". This self-priming region contains two intra-complementary regions separated by several, usually 3 to 5, nucleotides. The intra-complementary regions form a duplex, and the several nucleotides separating the intra-complementary regions form a loop. The 3' terminal base must be paired, and the region of complementarity must be sufficient to allow priming to occur. The resultant structure is referred to as a "hairpin". (Dattagupta, European Patent Application No. 427,073A2.) See FIG. 4. As shown, the 3'-terminus of the self-priming template serves as the primer.

It is also possible to design templates with primer complementary regions such that the primer complementary region of one template molecule will hybridize with the primer complementary region of another template molecule to form a duplexed primer complementary region. In this manner, one template serves as the primer for another, thus eliminating the need for a separate primer. These templates can be referred to as "primer/templates", since they serve both functions. See FIG. 5. As shown, using DNA primer/templates with a single 3'-ribonucleotide, the primer/template can be separated from the oligonucleotide product via alkaline hydrolysis and/or RNase.

The Primer

The primer can be synthesized using any of the aforementioned methods for synthesizing template. The primer can be either DNA or RNA, or a modified DNA or RNA. A particularly useful primer is a 3'-ribonucleotide primer which consists of DNA with several, preferably 1 to 4, ribonucleotides at or near (i.e. within 1 to 3 nucleotides of) its 3'-terminus. Preferably, the primer is a 3'-ribonucleotide primer consisting of DNA with a single ribonucleotide residue at its 3'-terminus. This type of primer has been utilized to prevent contamination during PCR (Walder et al., European Patent Application 496,483 A2). As used herein, 3'-ribonucleotide primers provide a convenient cleavage site for separation of the primer from the oligonucleotide product, since the internucleotide linkage which is 3' to a ribonucleotide residue is cleavable by chemical or enzymatic means.

The 3'-ribonucleotide primers are preferred, because they are capable of retaining their function after cleavage of the primer extension product to separate the primer from the oligonucleotide product. A primer which "retains its function" after cleavage is one which is capable of remaining hybridized to the same template, or hybridizing to a different template, to initiate a subsequent synthesis reaction.

Figure 6:
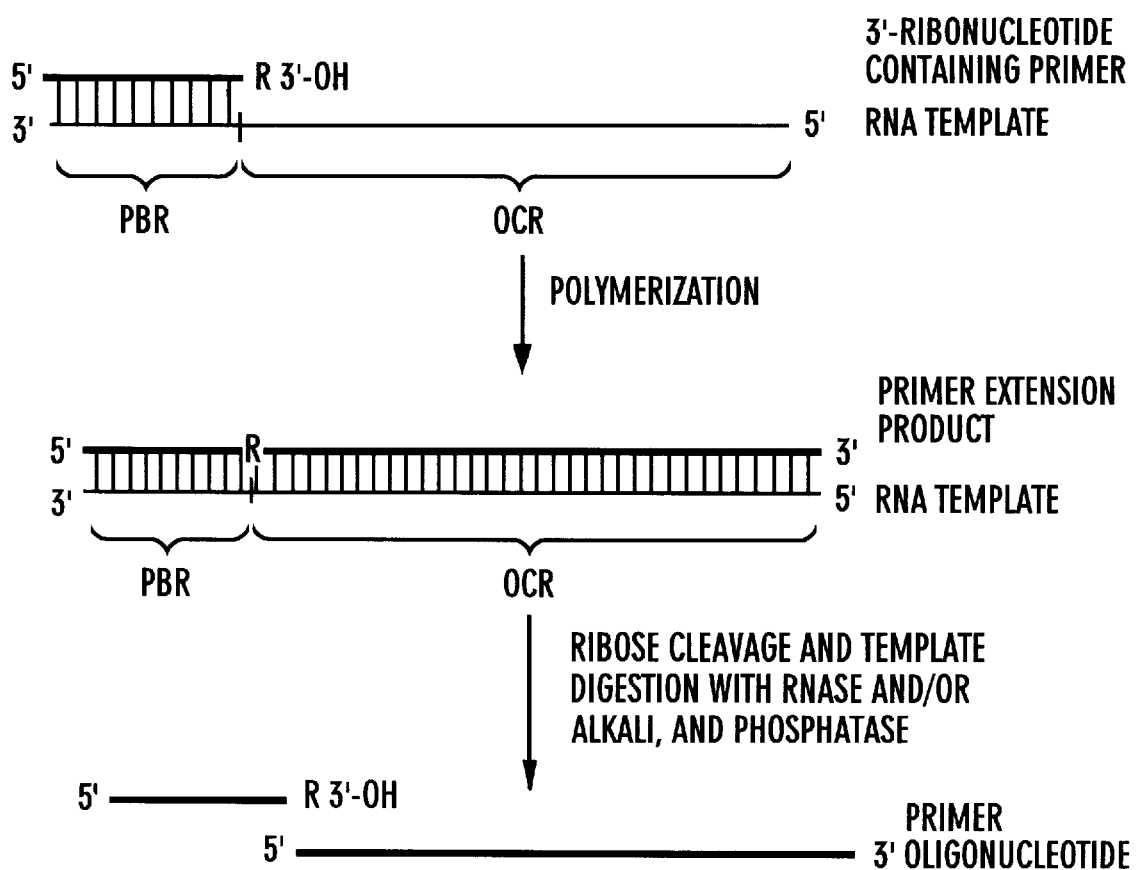
FIG. 6 illustrates the enzymatic synthesis of an oligonucleotide using a 3'-ribonucleotide primer.

Ribonucleotide-containing primers can be prepared using known methods of oligonucleotide synthesis. For example, see Walder, et al., supra. When a ribonucleotide-containing primer is used with an RNA template, cleavage of the primer extension product and digestion of the template can be accomplished simultaneously. See FIG. 6. See below for a more complete description of primer extension product cleavage and template digestion.

Another useful primer consists of an oligonucleotide which contains at least one deoxyuridine at the 3'-terminus. After synthesis of the primer extension product, the deoxyuridine residue can be excised by the combined action of a DNA glycosylase, followed by cleavage of the phosphate bond by an apurine/apyrimidine endonuclease (AP-endonuclease), and removal of the resultant exposed baseless sugar by an exonuclease. (See McGilvery, et al., *Biochemistry: A functional Approach*, W. B. Saunders Co., Philadelphia, Pa., 125–126 (1983).)

Formation of the Template-Primer Hybrid

Prior to oligonucleotide synthesis, a primer must be hybridized to the template. A template and primer combination should be used such that the primer binds to the primer binding region and not to any other region of the template. Thus, primers should be long enough and sufficiently complementary to the primer complementary region to form a stable duplex with it. The duplex thus formed allows the 3'-OH terminus of the primer to function as an initiation site for synthesis.

The primer and the template can be prehybridized prior to use, but are preferably added sequentially or simultaneously to the synthesis reaction mixture prior to addition of the polymerase. The hybridization conditions necessary to cause specific duplex formation between the primer and the template will most importantly depend on the specificity of the primer for the template's primer binding region, but will also depend to some degree on the heterogeneity of the nucleic acids present. The hybridization conditions must also be compatible with the polymerase enzyme being able to perform efficient and accurate synthesis. If chemically produced template is used wherein contamination by exogenous nucleic acids would be expected to be minimal, a wide range of hybridization conditions can be used to selectively hybridize the primer to the template. When the template is produced enzymatically in the presence of contaminating nucleic acids, hybridization conditions must be more stringent in order for selective hybridization of the primer and the template to occur. Stringency can be increased by any known method, such as lowering ionic strength, increasing washing temperatures, and/or using a denaturing agent.

Formation of the Primer Extension Product

The 3'-OH terminus of the primer in the primer-template hybrid serves as the initiation site for synthesis via sequential addition of dNTPs in the 5' to 3' direction. Alternatively, when a self-priming template is utilized, it is the 3'-OH terminus of the template's self-complementary region which serves as the initiation site for synthesis. The mixture of nucleotides to be used in the synthesis may contain either all unmodified, all modified, or both unmodified and modified dNTPs in appropriate ratios, such that a desired amount of incorporation of the modified dNTP is achieved. If a fully phosphorothioated oligonucleotide is to be synthesized, only dNTPαSs will be used. The modified dNTPs used may be the same or different, but are preferably the same (i.e. all methylphosphonates, all phosphorothioates, etc.) In addition, the mixture of dNTPs which are available for synthesis must contain all of the nucleotides necessary for formation of the primer extension product.

The choice of polymerase will depend on the template and the substrates used, and any requirements for specific reaction conditions (e.g. thermostable polymerases for high temperature reactions). Polymerases suitable for use with a variety of templates and substrates are well known in the art.

DNA-dependent DNA polymerases synthesize a complementary DNA copy of a DNA template. Examples of suitable DNA-dependent DNA polymerases include, but are not limited to: DNA polymerase I (Burgess, et al., Journal of Biol. Chem. 254: 6889–6893 (1979)); T4 polymerase (Romaniuk, et al., Journal of Biol. Chem. 257: 7684–7688 (1982)); and T7 polymerase (Brody, et al., Biochemistry 21: 2570 (1982)). Each of these polymerases can also be used to synthesize phosphorothioate oligonucleotides. All known DNA-dependent DNA polymerases require a complementary primer to initiate synthesis. Generally, the primer may be RNA or DNA, or a copolymer of RNA and DNA, to initiate synthesis. It is known that under suitable conditions certain DNA-dependent DNA polymerases may also synthesize a complementary DNA copy of an RNA template.

RNA-dependent DNA polymerases, also called reverse transcriptases, synthesize a complementary DNA copy of an RNA template. Examples of suitable RNA-dependent DNA polymerases include, but are not limited to avian myeloblastosis virus reverse transcriptase (Bartlett, et al., Journal of Biol. Chem. 257 (15): 8879–8854 (1982)). This enzyme, as well as other reverse transcriptases known in the art, is also capable of being used to synthesize phosphorothioate oligonucleotides. All known reverse transcriptases also have the ability to make a complementary DNA copy of a DNA template and are thus both RNA- and DNA-dependent DNA polymerases.

Cleavage of the Primer Extension Product

The primer extension product will necessarily have at least one cleavage site, and may have several equivalent or different cleavage sites. One cleavage site is necessary to separate the oligonucleotide product from the primer and, if the template's oligonucleotide complementary region consist of two or more subregions each having a sequence complementary to an individual oligonucleotide, the oligonucleotide product must contain cleavage sites for separation of the individual oligonucleotides.

Figure 7:
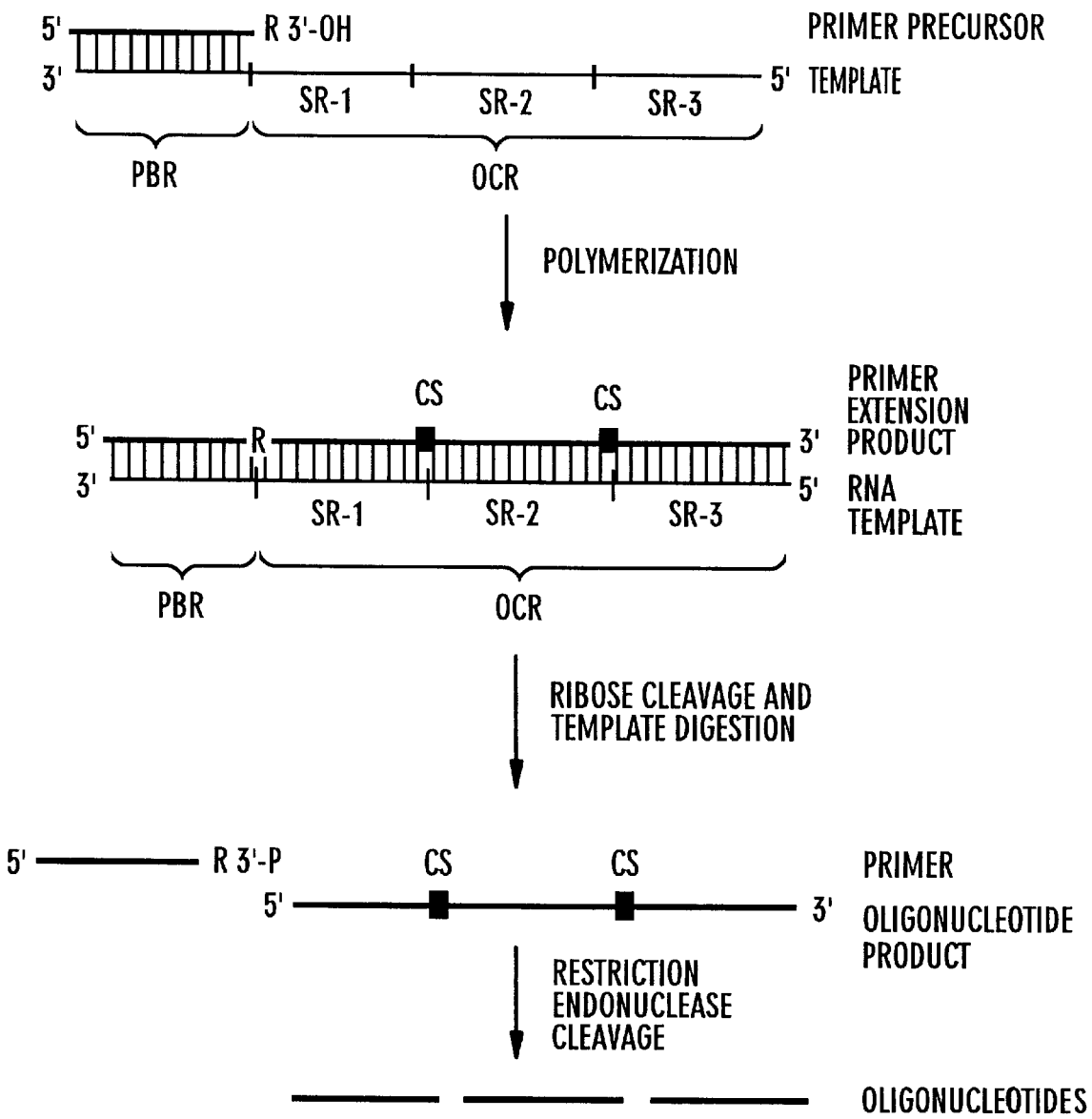
FIG. 7 illustrates the enzymatic synthesis of two or more oligonucleotides from a single template using a primer-extension product containing more than one type of cleavage site, one being the phosphate linkage 3' to a ribonucleotide residue which was introduced into the primer extension product by using a 3'-ribonucleotide primer, and the other being a restriction endonuclease recognition sequence.

When using a template to synthesize more than one individual oligonucleotide, it may be desirable to form a primer extension product with more than one type of cleavage site, one of which may be the phosphate linkage adjacent to a ribonucleotide residue which was formed by using a 3'-ribonucleotide primer, and the other of which may be a restriction endonuclease recognition sequence. In this manner, the primer extension product can be cleaved once to separate the primer, and then cleaved again (before or after purification) to separate the individual oligonucleotides from each other. See FIG. 7.

Different restriction sites can be incorporated into the primer extension product, each of which is recognized by a different restriction endonuclease, such as those identified in Example II below. An important aspect of the present invention is the discovery of several previously unknown restriction endonuclease/restriction sequence combinations which result in the cleavage of phosphorothioate oligonucleotides.

That these restriction sequences were capable of being recognized in phosphorothioate oligonucleotides and cleaved was an unexpected finding. Taylor, et al. (Nucleic Acids Research, 13(24): 8749–8764 (1985)) have reported that several restriction endonucleases, such as Alu I, are capable of cleaving partially phosphorothioated oligonucleotides. It was expected that there would be a correlation between the ability of restriction endonucleases to cleave partially phosphorothioated oligonucleotides and their ability to cleave fully phosphorothioated oligonucleotides. However, this was found not to be the case in all instances, and the efficiency of a restriction endonuclease to cleave fully phosphorothioated oligonucleotides could not be predicted based on previous results with partially phosphorothioated oligonucleotides. See Examples I to III.

In addition to the use of site-specific restriction endonucleases, if a 3'-ribonucleotide primer was used in conjunction with a DNA template, cleavage to separate the primer and the oligonucleotide product can be accomplished with alkaline hydrolysis, or by the use of an endonuclease, such as RNase.

RNase H's may contain either or both endonuclease or exonuclease activity. Avian myeloblastosis virus and Moloney murine leukemia virus reverse transcriptases contain an RNase H activity in addition to their polymerase activity. However, some cloned reverse transcriptases lack RNase H activity. There are also sources of RNase H available without an associated polymerase activity. Although the cleavage site of most RNase H's requires the presence of more than one ribonucleotide residue, RNase H's which are capable of cleaving a DNA strand containing a single internal ribonucleotide residue have been reported. (See Walder, et al., supra).

Cleavage of a primer extension product which is formed using a 3'-ribonucleotide primer occurs in the phosphate linkage(s) which is/are in the 3' direction from the ribonucleotide residue(s). Cleavage by alkali causes the formation of a mixture of 2'-, 3'- and 2',3'-cyclic phosphate ribonucleotides, which can then be "regenerated" by converting it back to a 3'-OH by alkaline phosphatase. Preferably, an RNase is used which results in reformation of a primer with a 3'-OH terminus. When the 3'-ribonucleotide primer consists of DNA with a single ribonucleotide residue at the 3' terminus, the regenerated or reformed primer will be identical to the original primer. Such primers are particularly preferred for this reason.

If a deoxyuridine-containing primer is used, cleavage can be accomplished by hydrolysis with a DNA glycosylase, followed by cleavage of the phosphate bond by an apurinic/apyrimidinic-endonuclease ("AP-endonuclease") and removal of the baseless sugar by an exonuclease. (See McGilvery, et al., *Biochemistry: A functional Approach*, supra.)

In instances where the primer and the oligonucleotide to be synthesized are both the same type of nucleic acid, for example both unmodified RNA or DNA, it is also possible for some of the nucleotides of the primer to be incorporated into the oligonucleotide product after cleavage of the primer extension product. In this situation, cleavage of the primer extension product occurs in the 5' direction from the original 3'-terminus of the primer, and one or more of the primer's nucleotides become incorporated into the 5' end of the oligonucleotide. Alternatively, it is possible for cleavage of the primer extension product to occur in the 3' direction from the original 3'-terminus of the primer. However, in both instances, the primer will not be able to be used in subsequent synthesis reactions.

In instances where a DNA primer/template with a single 3'-ribonucleotide is used, cleavage at the ribonucleotide residue as described above, followed by separation and purification of the oligonucleotide product, can result in a fully regenerated and reusable primer/template.

Digestion of the Template

The template is preferably capable of being digested after formation of the primer extension product. Using nucleases which will only recognize the double-stranded product formed after synthesis of the oligonucleotide, it is possible to digest the template only after formation of the primer extension product without digesting single-stranded template that has not yet directed the synthesis of a primer extension product. Digestion of the template can occur either before, simultaneously with or after cleavage of the primer extension product. Digestion of the template can serve two useful purposes; (1) synthesis reaction components can easily be recovered and reused; and (2) digestion leaves the oligonucleotide and the primer (or in the case of pre-cleavage digestion, the primer-extension product) in single-stranded form thus facilitating purification and/or separation from the synthesis reaction mixture.

If the template is DNA, digestion can be accomplished using a DNase. The oligonucleotide product can be protected from nuclease digestion by virtue of the incorporation of modified linkages during synthesis. If a modified primer is also used which is not digested by the DNase, the template can be selectively digested in the presence of primer, oligonucleotide and/or primer-extension product.

Preferably, the template is RNA, in which case digestion can easily be accomplished using alkaline hydrolysis and/or a suitable RNase.

EXAMPLE I

Determination of Restriction Endonuclease Effectiveness

The primer extension product can be cleaved with restriction endonucleases, provided that the template is designed to direct the synthesis of a primer extension product that contains a sequence which can be recognized by such an enzyme. Many restriction endonuclease recognition sequences are known in the art. (See *The Biochemistry of the Nucleic Acids:* Chapter 4, *Degradation and Modification of Nucleic Acids,* supra.)

Due to the resistance of many modified oligonucleotides to be recognized and thus cleaved by restriction endonucleases, it is necessary to prescreen restriction endonucleases prior to use in oligonucleotide synthesis for their ability to cleave a nucleic acid which contains the same modifications which are intended to be incorporated into the primer extension product. A screening method for phosphorothioate oligonucleotides follows.

Screening for restriction endonuclease activity was carried out according to the method described by Taylor, et al. (Nucleic Acids Research, 13(24): 8749–8764 (1985)). The substrate utilized was double-stranded M13 DNA with a completely native phosphodiester-linked (+) strand and a completely phosphorothioate-linked (−) strand. A control was prepared which contained DNA with native phosphodiester linkages in both strands. Each restriction endonuclease was tested for its ability to digest the substrate by incubating twenty units of each restriction endonuclease with 0.5 μg M13 DNA for 1 hour at the temperature and under the conditions described by the enzyme manufacturer for native phosphodiester DNA.

The restriction fragments which were formed using the assay substrate were compared to those formed using the control, and results were scored accordingly. These results are reported in Table 1. A result reported as "++" indicates that complete cleavage of bothe the control and test substrates was obtained using the specified reaction conditions. A result reported as + indicates that the restriction endonuclease was capable of cleaving the substrate, but less than complete cleavage occurred (i.e. "partial cleavage"). Even a result of only partial cleavage using this assay indicates that the restriction endonuclease should be suitable for use in the synthesis of phosphorothioate-containing oligonucleotides, since the cleavage reaction can easily be further optimized. An "effective amount" of restriction endonuclease is the amount necessary to effect cleavage under specified conditions.

TABLE 1

RESTRICTION ENDONUCLEASE STUDY USING DOUBLE STRANDED SUBSTRATE

| Enzyme* | Results | Recognition Sequence |
|---|---|---|
| AlwN I | + | 5'-CAGNNN/CTG-3' |
| BsaJ I | ++ | 5'-C/CNNGG-3' |
| Bsr I | ++ | 5'-ACTGGN/-3' |
| BstN I | ++ | 5'-CC/(A,T)GG-3' |
| Cla I | ++ | 5'-AT/CGAT-3' |
| Hae III | ++ | 5'-GG/CC-3' |
| HinP I | ++ | 5'-G/CGC-3' |
| Msp I | + | 5'-C/CGG-3' |
| Mva I | ++ | 5'-CC/(A,T)GG-3' |
| ScrF I | ++ | 5'-CC/(N)GG-3' |
| Taqα I | ++ | 5'-T/CGA-3' |

*All endonucleases except for Mva I were obtained from New England Biolabs, Inc., Beverly, MA. Mva I was obtained from Boehringer Mannheim, Indianapolis, IN.
N = A, T, C or G
/ = Location of cleavage
(A,T) = Either nucleotide

EXAMPLE II

Optimization of Restriction Endonuclease Conditions

The effects of reaction conditions on cleavage efficiency of several endonucleases were studied using the procedure described in Example I. In particular, the effects of substituting sodium acetate for NaCl, and $MnCl_2$ for $MgCl_2$ were studied in order to find conditions which favor cleavage. A similar optimization could be performed with any restriction endonuclease by using the conditions reported as optimal by the enzyme manufacturer and varying the type and amount of cations, anions, buffers, etc.

Each of the NaCl and $MgCl_2$ concentrations were kept at standard concentrations while varying the concentration of the other. Optimums for each are reported in Table 2 below. Then, while using the optimum concentration of NaCl, a varying amount of $MnCl_2$ was added as a substitute for $MgCl_2$. Likewise, while using the optimum concentration $MgCl_2$, a varying amount of sodium acetate was added as a substitute for NaCl. The ability of $MnCl_2$ and sodium acetate to substitute for $MgCl_2$ and NaCl, respectively, are also reported in Table 2.

TABLE 2

EFFECTS OF DIFFERENT REACTION CONDITIONS

| Enzyme | Conditions | NaCl, mM (0 to 400) | Sodium acetate, mM (0 to 400) | MgCl$_2$, mM (0.1 to 20) | MnCl$_2$, mM (0.1 to 10) |
|---|---|---|---|---|---|
| Hae III | Standard | 50 mM | | 10 mM | |
|  | Optimum | 0 mM | No effect | 2–5 mM | No effect |
| Taq$^\alpha$ I | Standard | 100 mM | | 10 mM | |
|  | Optimum | 50 mM | No effect | 1–2 mM | 0.5–2 mM |
| HinP I | Standard | 50 mM | | 10 mM | |
|  | Optimum | 50 mM | No effect | 10 mM | 2 mM |
| BstN I | Standard | 50 mM | | 10 mM | |
|  | Optimum | 0 mM | No effect | No effect | No effect |
| Mva I | Standard | 25 mM | | 10 mM | |
|  | Optimum | 100 mM | No effect | No effect | No effect |
| ScrF I | Standard | 100 mM | | 5 mM | |
|  | Optimum | 0–50 mM | 0–50 mM | 5–10 mM | 1 mM |

These results demonstrate that in most instances lowering the concentration of sodium chloride tended to increase the rate of phosphorothioate DNA cleavage. Similarly, lowering the magnesium chloride concentration was generally favorable to cleavage. Only in a few instances was any effect on cleavage observed by using MnCl$_2$ instead of MgCl$_2$, or sodium acetate instead of NaCl.

EXAMPLE III

Restriction Endonuclease Study using Single-Stranded Substrate

Figure 5:
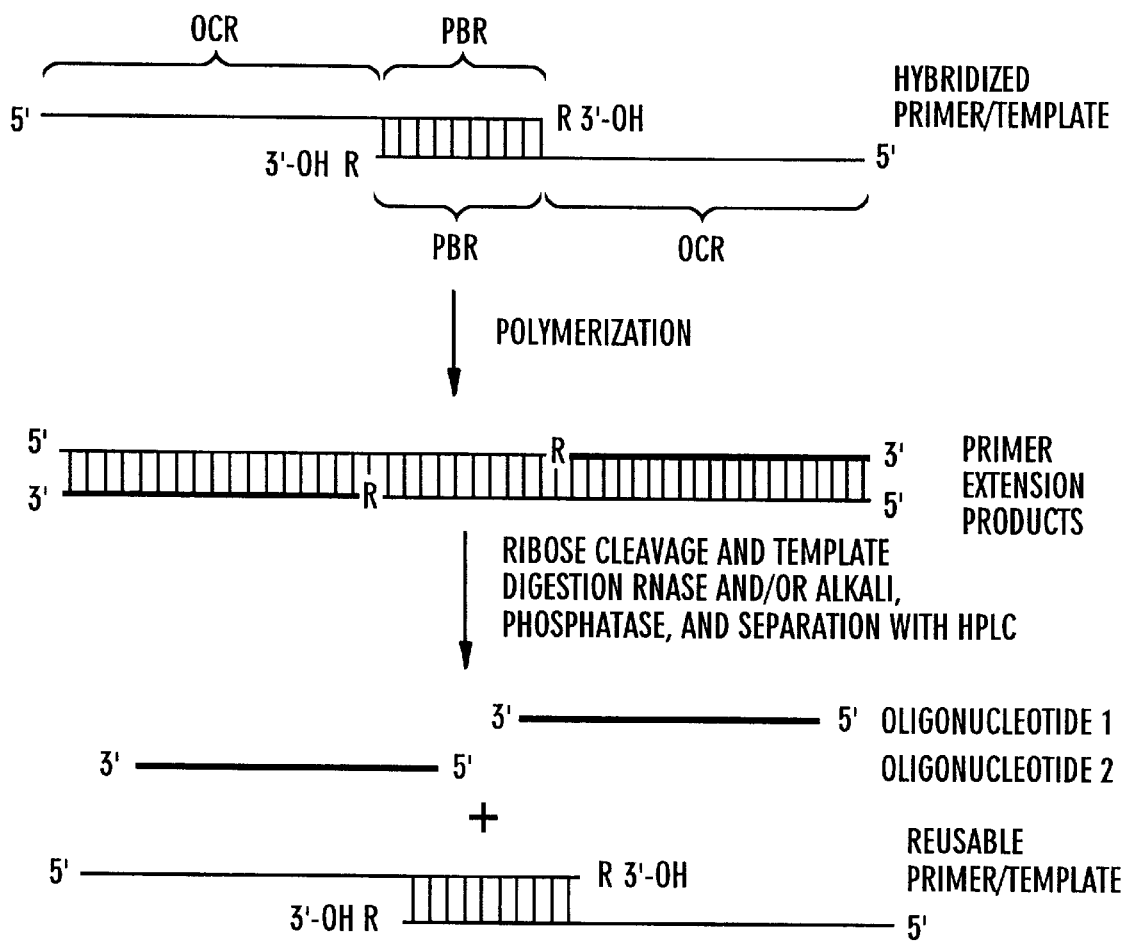
FIG. 5 illustrates the enzymatic synthesis of an oligonucleotide using a combined primer/template.

As shown in FIG. 5, it is possible to use a ribose-containing primer in combination with an RNA template to synthesize multiple oligonucleotides from a single template. Using alkali and/or RNase to cleave the primer extension product at the location of the ribose residue and to digest the template, a single-stranded product remains which must be cleaved. In order to test the ability of the restriction endonucleases from Example 1 to cleave a single-stranded target, an oligonucleotide substrate was chemically synthesized which contained restriction endonuclease recognition sequences for all of the enzymes to be tested. The sequence of this oligonucleotide is given in SEQ. ID. NO. 1 Using the standard conditions reported in Example 2, several enzymes were tested for their ability to cleave the single-stranded oligonucleotide substrate. The results are given below in Table 3:

TABLE 3

RESTRICTION ENDONUCLEASE STUDY USING SINGLE-STRANDED SUBSTRATE

| Enzyme | Results |
|---|---|
| BstN I | − |
| Hae III | + |
| HinP I | + |
| Mva I | − |
| ScrF I | ++ |
| Taq$^\alpha$ I | + |

Results reported as "+" indicate partial cleavage of the oligonucleotide substrate. Results reported as "++" indicate complete cleavage of the oligonucleotide substrate. Results reported as "−" indicate no significant cleavage. Under these cleavage conditions, either result indicates that the particular restriction endonuclease tested would be suitable for use.

EXAMPLE IV

Synthesis of an Oligonucleotide from an RNA Template

A. Preparation of Template

A template was chosen which would direct the synthesis of an antisense oligonucleotide which was complementary to the mRNA sequence given by SEQ. ID. NO. 2 encoding the HIV REV protein. (See Peterson, et al., Published PCT Application No. WO 95/03407.) Template was prepared by first chemically synthesizing an oligodeoxynucleotide having two subsequences; a T7 RNA polymerase self-complementary ("hairpin") promotor sequence (see SEQ. ID. NO. 3), and a sequence (see SEQ. ID. No. 4) which was complementary to the desired template. The sequence of this oligodeoxynucleotide is given by SEQ. ID No. 5.

The in vitro transcription from the oligodeoxynucleotide was carried out in a 20 ml reaction mixture containing 0.256 A$_{260}$ units of the oligodeoxynucleotide in 40 mM Tris (pH 8.0), 20 mM MgCl$_2$, 4 mM ATP, 4 mM GTP, 4 mM CTP, 4 mM UTP, 1 mM spermidine, 0.08% (w/v) polyethylene glycol (PEG) 8000, 0.01% (w/v) Triton X-100, 5 mM dithiothreitol (DTT), 50 µg/ml bovine serum albumin (BSA), 800 units of RNasin (Promega, Inc., Madison, Wis.), and 120,000 units of T7 RNA polymerase. The reaction mixture was incubated at 37° C. for approximately four hours, or until formation of a magnesium pyrophosphate precipitate was observed.

The template thus formed had the sequence given by SEQ. ID. NO. 6, and consisted of two subsequences; the primer binding region (SEQ. ID. NO. 7) and the oligonucleotide complementary region (SEQ. ID. NO. 8).

The template was isolated by chromatography as follows: The magnesium pyrophosphate precipitate was dissolved by the addition of EDTA to a final concentration of 20 mM. The reaction mixture was concentrated by precipitation with ethanol and redissolved in 10 ml of 100 mM triethylammonium acetate, pH 7.5. The redissolved RNA was isolated by reverse-phase HPLC on a C$_4$ column eluted with a gradient of acetonitrile. Fractions containing the RNA product were concentrated by ethanol precipitation.

B. Synthesis of the Oligonucleotide Product

A DNA primer (with a 3' terminus consisting of UC, where U is a ribonucleotide, and C is a deoxyribonucleotide) was used which had the sequence given by SEQ. ID. NO. 9. A 9 mL reaction mixture was prepared to contain 130 A$_{260}$ units of primer, 130 A$_{260}$ units of template, 50 mM Tris, pH 8.3, 75 mM KCl, 25 mM NaF, 3 mM MgCl2, 1 mM DTT, 100 µg/mL BSA, 200 units/ml RNasin, 1 mM dTTPαS, 1 mM dCTPαS and 1 mM dGTPαS (note that 1 mM dATPαS was not required because the desired oligonucleotide consisted only of C, G and T). Then, 3.6×10$^6$ units of Moloney murine leukemia virus (MMLV) reverse transcriptase was added, and the reaction mixture was incubated for twenty one hours at 37° C.

C. Purification of the Oligonucleotide Product

The resulting double stranded product consisting of the primer extension product (SEQ. ID. NO. 10) hybridized to the template was purified by extraction with toluene:phenol (9:1 v/v). The toluene:phenol phase was extracted three times with 10 mM Tris (pH 8.0), and the combined aqueous phases were concentrated by precipitation with ethanol. The ethanol precipitate was redissolved in 1.2 mL 10 mM Tris (pH 8.0), adjusted to 100 mM NaOH, then incubated for 60 minutes at 70° C. This alkaline hydrolysis had a dual function: 1) separating the oligonucleotide product from the primer by cleavage of the phosphodiester bond between the uridine of the primer and the cytidine of the oligonucleotide; and 2) digesting the RNA template.

The alkaline-treated material was neutralized with HCl, then the RNA template was treated with 12.5 μg E. coli RNase A for two hours to achieve more complete digestion of the RNA template. The oligonucleotide product (SEQ. ID. NO. 11) was concentrated by precipitation with ethanol, redissolved in 100 mM triethylammonium acetate, pH 7.5, and isolated by high pressure liquid chromatography on a $C_{18}$ reverse phase column eluted with acetonitrile using a 0.5% gradient. Peak fractions of the oligonucleotide product were pooled and concentrated by ethanol precipitation, redissolved in sterile phosphate buffered saline, and stored at −20° C.

D. Regeneration and Reuse of the Primer

The "used" primer from step C was reused in a subsequent synthesis according to steps A to C above and found to be 28% as active as an unused primer. Treatment of the used primer with calf intestine alkaline phosphatase resulted in the complete regeneration of the primer, as demonstrated by its reuse in a subsequent synthesis according to steps A to C with 100% the activity of an unused primer.

EXAMPLE V

Comparison of Oligonucleotide Product to Chemically Synthesized Oligonucleotide

In order to compare chemically synthesized oligonucleotides to enzymatically synthesized oligonucleotides, a phosphorothioate oligonucleotide was prepared using automated chemical synthesis (the "control") to have the same sequence as the oligonucleotide product from Example IV (the "product").

A. Comparison of Physiochemical Properties

The product appeared as a single band on a 20% denaturing polyacrylamide gel and had an electrophoretic mobility substantially identical to that of the control oligonucleotide. Additionally, the thermal denaturation curves of the product and the control were identical.

The product and the control were also compared using nuclear magnetic resonance spectroscopy calibrated with $H_3PO_4$. The signal obtained by both exhibited a peak at 55.639 ppm, and the product exhibited an upfield chemical shift which was consistent with the product containing phosphorothioate linkages with the Rp configuration.

B. Comparative Effect on p24 Production

The product was tested for effectiveness as an antisense agent in vitro and compared to the control. T-lymphocytes (SupT-1 from Advanced BioTechnologies, Inc., Columbia, Md.) were propagated in RPMI 1640 medium supplemented with 10% (v/v) fetal bovine serum and 50 μg/ml gentamicin sulfate at 37° C. in a humidified 5% $CO_2$ atmosphere. Only cell cultures having viable titers less than $2 \times 10^6$ cells/ml and viability in excess of 90%, as gauged by trypan blue exclusion, were used as hosts for acute infection.

Approximately $2.0 \times 10^6$ cells were pelleted by centrifugation at about 170 g for 8 minutes. The medium was removed and the cells were gently resuspended in fresh medium to a final concentration of about $1 \times 10^6$ cells/ml. HIV-1 strain IIIB ($1 \times 10^5$ $TCID_{50}$/ml; "TCID"=Tissue Culture Infective Dose), was added to the cells at a multiplicity of infection of 0.04 syncytium-forming units ("sfu") per cell (0.7 sfu=1.0 $TCID_{50}$). The virus and cell mixture was incubated for 2 hours at 37° C. in a humidified 5% $CO_2$ atmosphere, and then diluted to 10 ml with medium and pelleted by centrifugation at about 170 g for 8 minutes. The pelleted cells were washed three times with 10 ml of medium and then resuspended in medium to a concentration of $1 \times 10^5$ cells/ml.

Cells were dispensed in 100 μl volumes to round bottom wells of 96-well plates containing an equal volume of medium with various concentrations of product or control oligonucleotide, as well as a "no oligonucleotide" blank. Each concentration was tested at least twice. The plates were incubated at 37° C. in a humidified 5% $CO_2$ atmosphere. After 7 days, the cells in each culture were pelleted in situ by centrifuging the incubation plate at about 170 g for 8 minutes. One hundred μl of the supernatant from each well was transferred to a new 96-well plate and frozen at −80° C. for later p24 core antigen level determination.

The supernatants were allowed to thaw at room temperature and diluted to various levels in fresh medium. HIV-1 p24 antigen levels were determined using a capture ELISA purchased from Coulter Corporation (Hialeah, Fla.). The kinetic assay format was used and carried out according to the manufacturer's instructions. The effect on p24 antigen production was virtually the same between the product and the control.

C. Comparative Effect on Formation of Syncitia

The effect of the product and the control on plaque formation was determined as follows: HT-6C cells (clone 6C of Hela cells expressing CD4 from a recombinant retroviral vector, NIH AIDS Research and Reference Reagent Program) were maintained in 75 $cm^2$ tissue culture flasks in DMEM medium (Gibco BRL, Gaithersberg, Md.) supplemented with 10% fetal bovine serum, 100 units/ml penicillin, 100 μg/ml streptomycin, 2 mM glutamine at 37° C. in a humidified 5% $CO_2$ atmosphere. The cells were detached from the flasks with trypsin-EDTA (GibcoBRL, Gaithersberg, Md.), collected by centrifugation at 230 g and resuspended in the above medium. These cells were plated at $3.2 \times 10^4$ cells/well in 48-well tissue culture dishes and grown overnight at 37° C. in a humidified 5% $CO_2$ atmosphere.

To initiate an assay, the medium was removed from each well and 200 μl of HIV (100 to 200 plaque forming units) in DMEM medium supplemented with 4% (v/v) fetal bovine serum, 100 units/ml penicillin, 100 μg/ml streptomycin, 2 mM glutamine, 8 μg/ml DEAE dextran, and 0.5 μg/ml polybrene were added to each well. The dishes were incubated at 37° C. in a humidified 5% $CO_2$ atmosphere. After 2 hours, 800 μl of medium containing various concentrations of product or control was added to wells, and the dishes were each incubated at 37° C. in a humidified 5% $CO_2$ atmosphere for three days. The medium from each well was then removed and 1 ml of 100% methanol was added to each well to fix the cells to the dishes. After 15 minutes, the methanol was removed and 0.5 ml of 0.3% (w/v) crystal violet stain dissolved in phosphate buffered saline was added to each well. After 5 minutes, the wells were rinsed with water, drained and allowed to dry. The number of syncitia (dark staining giant cells) in each well were counted using microscopic examination. The percent reduction in syncitium formation resulting from treatment with various concentrations of the oligonucleotide product and the control oligonucleotide were virtually the same.

EXAMPLE VI

Synthesis of an Oligonucleotide using a Self-Priming RNA Template

A. Preparation of Template

A template was chosen which would direct the synthesis of an antisense oligonucleotide which was complementary to an mRNA sequence (SEQ. ID No. 2) encoding the HIV REV protein. (See Peterson, et al., supra.) Template was prepared by first chemically synthesizing an oligodeoxynucleotide having three subsequences given in 5' to 3' order: a T7 RNA polymerase self-complementary ("hairpin") promotor sequence (SEQ. ID. NO. 12); and a sequence which was complementary to the desired self-priming template (SEQ. ID. NO. 13). The sequence of this oligodeoxynucleotide, which terminated in a 5' non-nucleotide "RXL" linker, is given by SEQ. ID No. 14. (For the precise structure of the RXL linker, see Arnold, et al., PCT WO 89/02439, linker reagent 23 of Example 8(a), incorporated herein by reference).

The in vitro transcription from the oligodeoxynucleotide was carried out in a 2.0 ml reaction mixture containing 0.252 $A_{260}$ units of the oligodeoxynucleotide in 40 mM Tris (pH 8.0), 20 mM $MgCl_{12}$, 4 mM ATP, 4 mM GTP, 4 mM CTP, 4 mM UTP, 1 mM spermidine, 0.08% (w/v) polyethylene glycol (PEG) 8000, 0.01% (w/v) Triton X-100, 5 mM dithiothreitol (DTT), 5 µg/mL bovine serum albumin (BSA), 100 units of RNasin (Promega, Inc., Madison, Wis.), and 24,000 units of T7 RNA polymerase. The reaction mixture was incubated at 37° C. for approximately four hours, or until formation of a magnesium pyrophosphate precipitate was observed.

The self-priming template thus formed had the sequence given by SEQ. ID. NO. 15, and consisted of two subsequences in 5' to 3' order; the oligonucleotide complementary region (SEQ. ID. NO. 16) and the self-priming region (SEQ. ID. NO. 17).

The template was isolated by chromatography as follows: The magnesium pyrophosphate precipitate was dissolved by the addition of EDTA to a final concentration of 20 mM. The reaction mixture was concentrated with ethanol, and redissolved in 0.1M triethylammonium acetate, pH 7.5. The redissolved RNA was applied to a Sep-Pak $C_{18}$ cartridge (Millipore Waters, Milford, Mass.) and washed with 0.1M triethylammonium acetate, pH 7.5. The template was eluted with 70% methanol in water, concentrated by vacuum evaporation and redissolved in 0.1M triethylammonium acetate, pH 7.5. The RNA transcript was further purified by high pressure liquid chromatography.

B. Synthesis of Oligonucleotide Product

A 1 mL reaction mixture was prepared to contain 7.45 $A_{260}$ units of self-priming template, 50 mM Tris, pH 8.3, 75 mM KCl, 3 mM $MgCl_2$, 336 units/ml RNasin, 3 mM dTTPαS, 3 mM dCTPαS and 3 mM dGTPαS (note that 1 mM dATPαS was not required because the desired oligonucleotide consisted only of C, G and T). Then, 1.3×10⁶ units of Moloney murine leukemia virus (MMLV) reverse transcriptase was added, and the reaction mixture was incubated for seven hours at 37° C.

EXAMPLE VII

Synthesis of a Plurality of Oligonucleotides from a Single Template

A. Preparation of Template

A template was chosen which would direct the synthesis of an antisense oligonucleotide which was complementary to an MRNA sequence (SEQ. ID No. 18) encoding the HIV REV protein. (See Peterson, et al., supra.) Template was prepared by first chemically synthesizing an oligodeoxynucleotide having two subsequences; a T7 RNA polymerase promotor sequence (SEQ. ID. No. 19), and a sequence (SEQ. ID. No. 20) which was complementary to the desired template, and which consisted of three repeated subsequences. The sequence of this oligodeoxynucleotide is given by SEQ. ID No. 21.

The in vitro transcription from the oligodeoxynucleotide was carried out in a 0.1 ml reaction mixture containing 0.003 $A_{260}$ units of the oligodeoxynucleotide in 40 mM Tris (pH 8.0), 20 mM MgCl2, 4 mM ATP, 4 mM GTP, 4 mM CTP, 4 mM UTP, 1 mM spermidine, 0.08% (w/v) polyethylene glycol (PEG) 8000, 0.01% (w/v) Triton X-100, 5 mM dithiothreitol (DTT), 50 µg/mL bovine serum albumin (BSA), and 600 units of T7 RNA polymerase. The reaction mixture was incubated at 37° C. for three hours. The reaction was stopped by heating for 10 minutes at 70° C. After cooling to 0° C., 80 units of RNasin (Promega, Inc., Madison, Wis.) were added.

The template thus formed had the sequence given by SEQ. ID. NO. 22.

B. Synthesis of Oligonucleotide Product

The template was reverse transcribed without further purification. A 10 µl aliquot of the reaction mixture was added to a synthesis reaction mixture containing 19 ng $dT_{10}$ primer, 50 mM Tris HCl (pH 8.3), 75 mM KCl, 3 mM MgCl2, 2 mM dATPαS, 2 mM dTTPαS, 2 mM dGTPαS, 2 mM dCTPαS, and 80 units of RNasin. To this synthesis reaction mixture was added RNase H free MMLV reverse transcriptase (Gibco BRL, Bethesda, Md.) to a total volume of 100 µl. This oligonucleotide product precursor thus formed was purified on a NENSORB 20 cartridge (DuPont NEN, Boston, Mass.) according to manufacturer's instructions. This was followed by cleavage into individual oligonucleotides by treatment with 35 units of Hae III (New England Biolabs, Beverly, Mass.) and 1 µg RNase (DNase-free, Boehringer-Mannheim, Indianapolis, Ind.) in Restriction Buffer 2 (New England Biolabs, Beverly, Mass.) for 22 hours at 37° C. The sequence of the oligonucleotide product is given in SEQ. ID. NO. 23.

Although the invention has been described in terms of specific embodiments, many modifications and variations of the present invention are possible in light of the teachings. It is, therefore, to be understood that within the scope of the appended claims the invention may be practiced otherwise than as specifically described.

We claim:

1. A method of synthesizing one or more oligonucleotides comprising the steps of:
   (a) providing a nucleic acid template comprising a primer binding region and an oligonucleotide complementary region located 5' to said primer binding region, said primer binding region being complementary to a nucleic acid primer and said oligonucleotide complementary region comprising one or more subregions, each said subregion being complementary to one of said oligonucleotides to be synthesized, wherein said template is used to direct the synthesis of a primer extension product comprising (i) an oligonucleotide product comprising said oligonucleotides and one or more cleavage sites when said oligonucleotide product comprises two or more of said oligonucleotides, each said cleavage site separating a pair of said oligonucleotides positioned adjacent to one another on said oligonucleotide product, (ii) said primer, and (iii) a cleavage site separating said primer from said oligonucleotide product;
   (b) contacting said template with said primer under conditions such that said primer is able to hybridize to the primer binding region of said template to form a template-primer hybrid, wherein said primer comprises DNA and a ribonucleotide located at the 3'-terminus of said primer;

(c) incubating said template-primer hybrid in the presence of at least one DNA polymerase under conditions such that DNA synthesis occurs to form a primer extension product;

(d) cleaving said primer extension product to separate said primer from said oligonucleotide product by hydrolyzing the internucleotide phosphate linkage in the 3' direction from said ribonucleotide; and (e) repeating steps (b)–(d) at least once using the primer from step (d).

2. A method of synthesizing one or more oligonucleotides comprising the steps of:

(a) providing a nucleic acid template comprising a primer binding region and an oligonucleotide complementary region located 5' to said primer binding region, said primer binding region being complementary to a nucleic acid primer and said oligonucleotide complementary region comprising one or more subregions, each said subregion being complementary to one of said oligonucleotide to be synthesized, wherein said template is used to direct the synthesis of a primer extension product comprising (i) an oligonucleotide product comprising said oligonucleotides and one or more cleavage sites when said oligonucleotide product comprises two or more of said oligonucleotides, each said cleavage site separating a pair of said oligonucleotides positioned adjacent to one another on said oligonucleotide product, (ii) said primer, and (iii) a cleavage site separating said primer from said oligonucleotide product;

(b) contacting said template with said primer under conditions such that said primer is able to hybridize to the primer binding region of said template to form a template-primer hybrid, wherein said primer comprises DNA and a ribonucleotide located near the 3'-terminus of said primer;

(c) incubating said template-primer hybrid in the presence of at least one DNA polymerase under conditions such that DNA synthesis occurs to form a primer extension product;

(d) cleaving said primer extension product to separate at least a portion of said primer from said oligonucleotide product by hydrolyzing the internucleotide phosphate linkage in the 3'- direction from said ribonucleotide; and (e) repeating steps (b)–(d) at least once using the primer separated in step (d) in place of said primer of step (b), wherein the primer separated in step (d) is the same as or different than said primer of step (b).

3. The method of claim 1 or 2, wherein said oligonucleotides are modified.

4. The method of claim 1 or 2, wherein said oligonucleotides are phosphorothioate-containing oligonucleotides.

5. The method of claim 1 or 2, wherein said template is RNA.

6. The method of claim 1 or 2, wherein said template is DNA.

7. The method of claim 1 or 2, wherein the oligonucleotide complementary region comprises more than one subregion, and further wherein said template is used to direct the synthesis of a primer extension product which can be cleaved to form two or more oligonucleotides having the same or different lengths and/or sequences.

8. The method of claim 7, wherein said primer extension product comprises at least one restriction endonuclease recognition sequence, and wherein said oligonucleotide product is cleaved to separate said oligonucleotides from each other using a restriction endonuclease able to recognize said restriction endonuclease recognition sequence.

9. The method of claim 1 or 2, wherein said primer is separated from said oligonucleotide product using alkaline hydrolysis.

10. The method of claim 1 or 2, wherein said primer is separated from said oligonucleotide product using an RNase H activity.

11. The method of claim 1 or 2, wherein said template and said primer are contained on the same nucleic acid strand, such that said template is a self-priming template comprising a self-complementary region and an oligonucleotide complementary region, and wherein said primer comprises the 3'-terminus of said self-complementary region.

12. The method of claim 5, wherein said template is digested before, simultaneous with, or subsequent to step (d) using alkaline hydrolyis, so that said template is separated from said primer extension product.

13. The method of claim 3, wherein said oligonucleotides are phosphorothioate oligonucleotides.

14. The method of claim 2, wherein said oligonucleotides are modified.

15. The method of claim 14, wherein said oligonucleotides are phosphorothioate-containing oligonucleotides.

16. The method of claim 14, wherein said oligonucleotides are phosphorothioate oligonucleotides.

17. The method of claim 8, wherein said primer extension product comprises at least two different restriction endonuclease recognition sequences, and wherein said primer extension product is cleaved to separate said one or more oligonucleotides from each other using restriction endonucleases able to recognize said recognition sequences.

18. The method of claim 1 or 2, wherein said primer extension product comprises at least one restriction endonuclease recognition sequence, and wherein said primer extension product is cleaved to separate said primer from said oligonucleotide product using a restriction endonuclease able to recognize said recognition sequence.

19. The method of claim 5, wherein said template is digested before, simultaneous with, or subsequent to step (d) using an RNase H activity, so that said template is separated from said primer extension product.

20. The method of claim 5, wherein said template is digested before, simultaneous with, or subsequent to step (d) using a DNase, so that said template is separated from said primer extension product.

21. The method of claim 1 or 2, wherein said primer is separated from said oligonucleotide product using an RNase H activity.

22. The method of claim 1 or 2, wherein step (a) further includes providing a second nucleic acid template comprising a primer binding region and an oligonucleotide complementary region located 5' of the primer binding region of said second template, and further wherein the primer complementary region of said second template comprises the primer of said first template.

23. The method of claim 3, wherein said cleavage sites separating said adjacent oligonucleotides and/or said cleavage site separating said primer from said oligonucleotide product contain a modified phosphodiester linkage.

24. The method of claim 23, wherein said modified phosphodiester linkage is a phosphorothioate linkage.

25. The method of claim 4, wherein said cleavage sites separating said adjacent oligonucleotides and/or said cleavage site separating said primer from said oligonuclcotide product contain a modified phosphodiester linkage.

26. The method of claim 25, wherein said modified phosphodiester linkage is a phosphorothioate linkage.

27. The method of claim 13, wherein said cleavage sites separating said adjacent oligonucleotides and/or said cleavage site separating said primer from said oligonucleotide product contain a modified phosphodiester linkage.

28. The method of claim 27, wherein said modified phosphodiester linkage is a phosphorothioate linkage.

29. The method of claim 14, wherein said cleavage sites separating said adjacent oligonucleotides and/or said cleavage site separating said primer from said oligonucleotide product contain a modified phosphodiester linkage.

30. The method of claim 29, wherein said modified phosphodiester linkage is a phosphorothioate linkage.

31. The method of claim 15, wherein said cleavage sites separating said adjacent oligonucleotides and/or said cleavage site separating said primer from said oligonucleotide product contain a modified phosphodiester linkage.

32. The method of claim 31, wherein said modified phosphodiester linkage is a phosphorothioate linkage.

33. The method of claim 16, wherein said cleavage sites separating said adjacent oligonucleotides and/or said cleavage site separating said primer from said oligonucleotide product contain a modified phosphodiester linkage.

34. The method of claim 33, wherein said modified phosphodiester linkage is a phosphorothioate linkage.

35. The method of claim 13, wherein said oligonucleotides are chirally pure.

36. The method of claim 16, wherein said oligonucleotides are chirally pure.

37. The method of claim 1 or 2, wherein said oligonucleotide is separated and purified.

38. The method of claim 12, 19 or 20, wherein said oligonucleotide is separated and purified.

* * * * *